US00PP08684P

United States Patent [19]

Smalley et al.

[11] Patent Number: Plant 8,684

[45] Date of Patent: Apr. 12, 1994

[54] ELM TREE NAMED NEW HORIZON

[75] Inventors: Eugene B. Smalley, Cottage Grove; Raymond P. Guries, Oregon, both of Wis.

[73] Assignee: Wisconsin Alumni Research Foundation, Madison, Wis.

[21] Appl. No.: 900,864

[22] Filed: Jun. 18, 1992

[51] Int. Cl.[5] ..... A01H 5/00

[52] U.S. Cl. ..... Plt./53.3

[58] Field of Search ..... Plt. 53.3

*Primary Examiner*—James R. Feyrer

*Attorney, Agent, or Firm*—Quarles & Brady

[57] ABSTRACT

A new interspecific hybrid elm tree of *U. japonica* × *U. pumila* which expresses exceptional vigor when young, attractive crown shape, compact habit, dense foliage concentration, resistance to branch shearing forces of weather, and a high level of resistance to common elm diseases and elm leaf minor to which previous similar hybrid trees and siblings have shown susceptibility.

6 Drawing Sheets

The present invention relates to a new and distinct variety of elm tree which is characterized by its high vigor and upright habit as well as resistance to Dutch elm disease caused by *Ophiostoma ulmi* (Buisman) Nannf.

Figure 4:
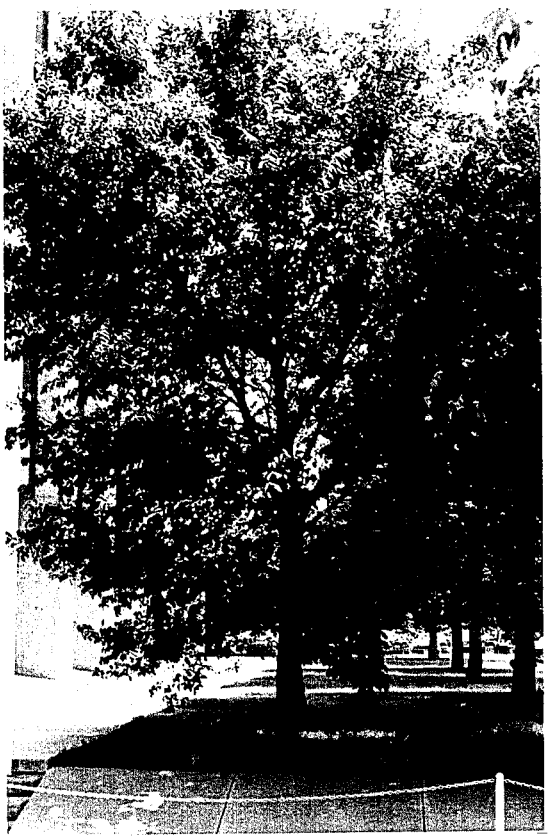

This new elm variety was produced from a breeding program intended to utilize the Dutch elm resistant Asian elm stock to create elm trees having a form suitable for the American horticultural industry. The "New Horizon" elm is a hardy cultivar which possesses an upright form, high disease resistance, and a compact growth habit, which makes it ideal for an urban landscape and street tree plant environments. New Horizon tends to develop a main central leader with primary scaffold branches at about 30° off the vertical as shown in FIG. 4. The lateral scaffold branches become suppressed as the tree develops. However, at wide spacing these develop more vigorously.

Figure 1:
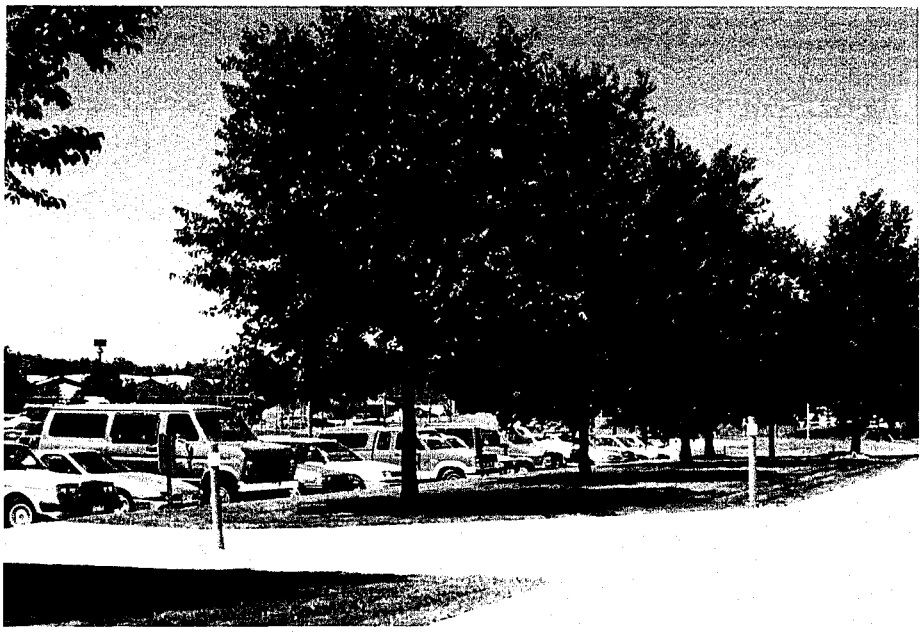
Figure 2:
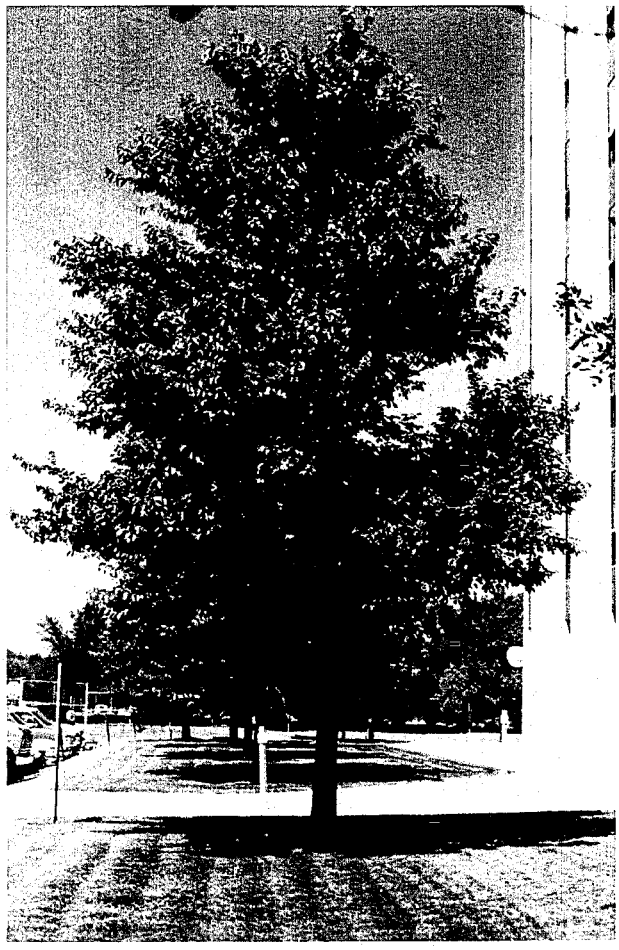
Figure 3:
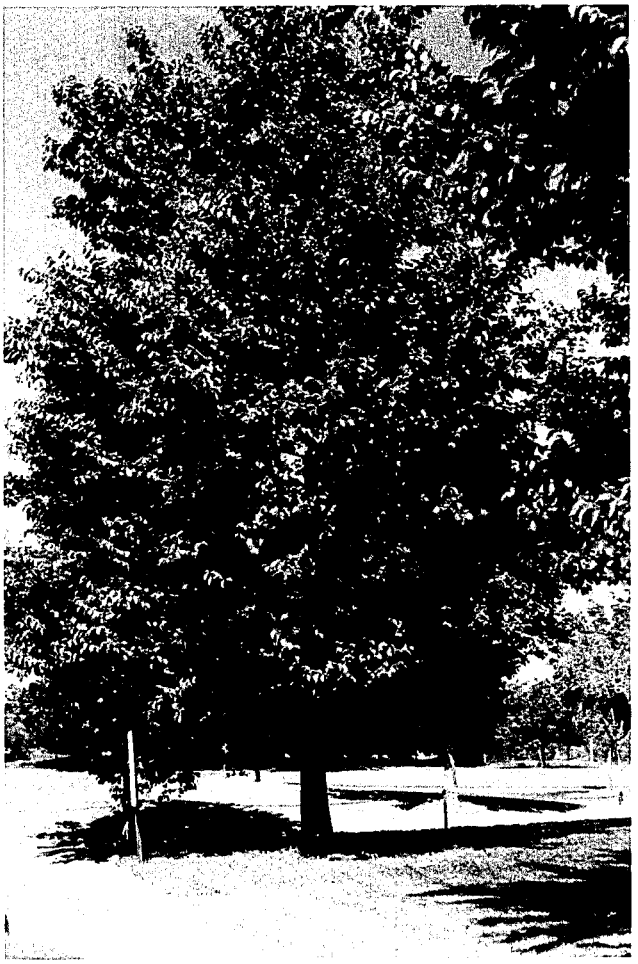
Figure 5:
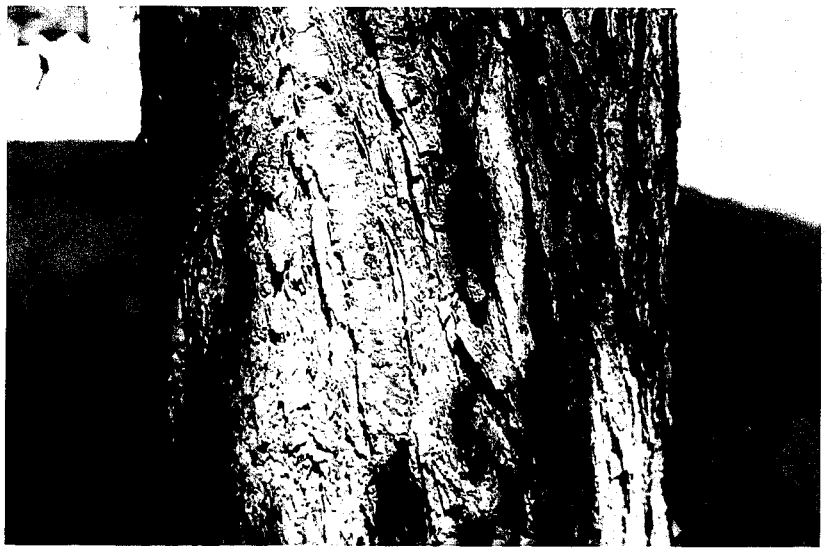
Figure 6:
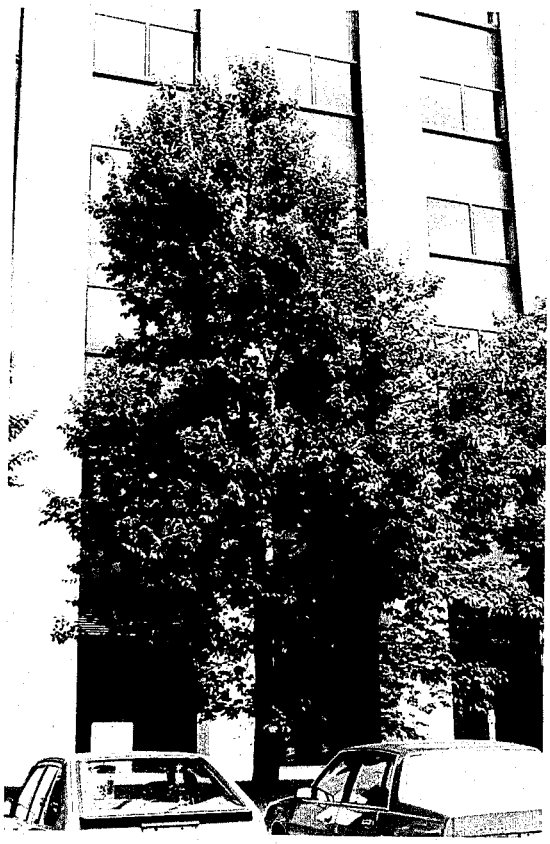

The accompanying photographs comprising FIGS. 1, 2 and 3 show three different specimens of the tree each in a relatively spacious location. FIG. 4 shows the branching habit of the claimed variety. FIG. 5 shows the bark of the claimed variety. FIG. 6 provides another view of the New Horizon crown. Note that the tree remains compact and tends to be very upright and not as spreading as other elm varieties.

Origin

The "New Horizon" elms are all ramets of a single disease-resistant individual selected from the surviving seedling progeny produced from a controlled pollination between a defined Dutch elm disease resistant *U. japonica* selection and a vigorous *U. pumila* seedling. The *U. pumila* seedling came from a lot of seedlings of ambiguous origin, but probably originating from *U. pumila* street trees in Yankton, S.D. During the period of origin of those trees, a nursery in Yankton, S.D., was a major collector and distributor of *U. pumila* seeds and liners to North Central nurseries. The seed collected from Yankton trees had previously given rise to so-called "disease-resistant hybrid elm" selections marketed for several decades by various North American nurseries. These hybrids are putative natural hybrids and back-crosses between *U. pumila* and *U. rubra* and their naturalized progeny. By contrast, the "New Horizon" elm is a cross to a specific *U. japonica* individual selected for its high disease resistance.

Description

Soon after planting, "New Horizon" develops a strong central leader with relatively short lateral branches. The trees are vigorous and develop well in exposed situations, providing an attractive accent to otherwise harsh building surfaces. Under controlled temperatures (24° C.) in a plant growth chamber, ramets of "New Horizon" over an 80 day growth period grew at a rate of 1.14 centimeters per day, which is a rate 9.2% faster than trees of the "Sapporo Autumn Gold" variety and 12.4% faster than "Regal" elm trees. This makes fast growth a characteristic of the "New Horizon" elm. Young trees growing at a wide spacing are densely foliated. This uniform, compact growth habit makes it an excellent choice for boulevard plantings or urban plantings associated with low density buildings such as shopping malls, condominiums and modern housing developments.

New spring growth of a "New Horizon" elm is fern green in color (g62/1) (Royal Horticultural Society RHS Color Chart (1966)). The mature leaves exposed to full sun are glaborous, dark "parsley green" (00962) on the upper side and "spinach green" (0960/3) ranging from slight downy-pubescent to glabrous. Pubescence tends to be a juvenile characteristic found mainly on the more vigorous shoots, while leaves on the less vigorous branches are always glabrous. All phases of pubescence can be found in a single tree. Mature leaves are ovate-elliptical, unequal at the base, sharply acuminate at the tip, and double serrate at the margins. Leaves are 8 to 9 centimeters long (mean 8.5) and 3 to 6 centimeters wide (mean 4.9). The leaf petioles vary from 0.8 to 1.5 centimeters in length. Fall coloration is not a distinctive feature of tree; leaf abscission takes place in late September or early October in South Central Wisconsin. New Horizon, like other elm species in Madison, Wis., begin their leaf bud-break on or about May 1. This widely variable date depends upon the rate of spring warm-up, which fluctuates in this climate. The bud-break characteristics of New Horizon are similar to native American elms.

Apical dominance is moderate, but still results in limited side branching on the developing shoot of the current season's growth. Current season's side branches, however, tend to be retained as leafy, but subordinate growth the following growing season. The result of this pattern of growth is a stiff upright growth with dense foliation. The foliar canopy of New Horizon is at least as dense as that of other native American elm trees.

The bark develops into its mature form at 6 to 8 years of age and develops in varying shades of brown slowly aging to gray. The bark color is similar to that of native American elms, though somewhat redder. The red color is presumably derived from the parental Japanese elm. At maturity the bark cracks with broad, flat, scaly ridges. See FIG. 5 which depicts the mature bark of New Horizon.

The original tree of the New Horizon variety is very large in spite of its location in a dense planting of elm siblings. The floral and seeding characeristics are not distinctive, but resemble its *U. japonica* ancestry. Seed production in older trees is sparse, creating minimal litter problems.

It is believed that, in a widely spaced planting, New Horizon elm trees might achieve heights of 75 feet or more. New Horizon elms are consistently taller than they are wide, in the crown, as shown clearly in FIGS. 2, 3 and 6.

New Horizon produces seeds on monoecious flowers which contain both stamens and pistils. Seed production is sparse, as it is in the maternal Japanese parent. Seed size also resembles the maternal parent, rather than the larger seed of the paternal parent. The seed density is a function of having fewer flowers than other elms. Seeds are shed in early June.

It is not known whether New Horizon is self or cross infertile. Nectria canker has not been observed on New Horizon.

Disease Resistance

The "New Horizon" elm has exhibited superior resistance to *O. ulmi*, following screening for DED resistance using the methods described in Lester, *Search* 8:39–40 (1978); and Sinclair, et al., *Plant Disease Reporter* 58:784–788 (1974). The results of this screening for resistance to Dutch elm disease of this variety in conjunction with a number of sibling hybrid elm clones is summarized in Table I. The clone number 917 represents the "New Horizon" elm.

TABLE I

Seasonal susceptibility of selected elm clones to Dutch elm disease
Percent crown damage at final reading (8/18/81)

| Elm species | Clone number | Dates of inoculation of three year old trees 5/19 | 5/26 | 6/02 | 6/09 | 6/16 |
|---|---|---|---|---|---|---|
| pj × h | 909 | 0.2 | 0.0 | 1.7 | 3.3 | 1.7 |
| pj × h | 910 | 13.5 | 6.7 | 5.0 | 0.0 | 0.0 |
| pj × h | 911 | 18.0 | 5.8 | 1.8 | 0.0 | 0.0 |
| pj × h | 912 | 0.0 | 0.0 | 0.0 | 0.0 | 0.0 |
| pj × h | 913 | 0.0 | 0.0 | 0.0 | 0.0 | 0.0 |
| pj × h | 914 | 0.0 | 0.0 | 0.0 | 0.0 | 0.0 |
| j × pj | 918 | 0.0 | 0.0 | 0.0 | 0.0 | 0.0 |
| j × p | 916 | 0.0 | 0.6 | 0.0 | 0.0 | 0.0 |
| j × p | 917 | 0.0 | 0.0 | 0.0 | 0.0 | 0.3 |

| Elm species | Clone number | Dates of inoculation of three year old trees 6/23 | 6/30 | 7/07 | 7/21 | 8/04 |
|---|---|---|---|---|---|---|
| pj × h | 909 | 0.0 | nd | 0.0 | 0.0 | nd |
| pj × h | 910 | 0.0 | 0.0 | 0.0 | 0.0 | 0.0 |
| pj × h | 911 | 14.3 | 0.0 | 0.0 | 0.0 | 0.0 |
| pj × h | 912 | 0.0 | 0.0 | 0.0 | 6.4 | 0.0 |
| pj × h | 913 | 0.0 | 0.0 | 0.0 | 12.0 | 0.0 |
| pj × h | 914 | 0.0 | nd | 0.0 | 0.0 | 0.0 |
| j × pj | 918 | 3.8 | 0.0 | 0.0 | 0.0 | 0.1 |
| j × p | 916 | 0.0 | 0.0 | 0.0 | 0.0 | 0.0 |
| j × p | 917 | 0.0 | 0.0 | 0.0 | 0.0 | 0.0 |

p = *U. pumila*
j = *U. japonica*
h = *U. hollandica*

When testing elm seedlings for resistance to *O. ulmi*, seedlings are grown for one year in outdoor seed beds or in Roottrainers (Spencer-Le Maire Industries) in the greenhouse, then transplanted into field locations in the second or third season. The trees are maintained under clean cultivation, and are artificially inoculated with *O. ulmi* in the third or fourth year. Trees with inoculated in one-year-old wood in the tree's upper crown with an inoculum containing approximately $10^6$ spores per ml. Survivors of this procedure are re-inoculated in subsequent years. As a final test (called the "seasonal susceptibility trial"), selected resistant individuals are clonally propagated and grown in replicated field plantings for two or more years. Different individuals of each clone are then inoculated periodically during the growing season to define a seasonal pattern of susceptibility. In this test, the inoculum consisted of mixed conidial suspensions from ten different isolated of the fungus from different North American locations. Observations on disease development are then recorded periodically throughout the year following inoculation. The "New Horizon" cultivar described here possesses superior resistance to *O. ulmi* disease. See Table I, in which the "New Horizon" trees are identified as clone 917.

Asexual Reproduction

The "New Horizon" elm can be propagated from root segments allowed to sprout in the greenhouse in moist sphagnum peat and sand. Greenwood cuttings are taken from the sprouts and dipped in commercial rooting hormone. Such cuttings can then be transplanted as rooted cuttings after approximately twenty days in a perlite-peat rooting medium under fine intermittent mist. Propagation by grafting or budding should be avoided because of the uncertainties relative to the suitable root stocks and possible long-term incompatibilities.

New Horizon elm was asexually reproduced from root cuttings of clone 917, obtained as described, on the campus of the University of Wisconsin in Madison, Wis.

Other Characteristics

Trees of the elm variety "New Horizon" are highly tolerant to *Verticillium dahliae* Kleb., the causal agent of Verticillium wilt disease. Planting in soils known to have been heavily infested have remained symptomless even when nearby trees of susceptible species developed severe Verticillium wilt symptoms. The variety also appears to have very limited susceptibility to black leaf spot disease, caused by *Stegophora ulmea*. Ice storms or severe winds have not produced injury on the parent tree or in the experimental plantings of the "New Horizon" elms, even were adjacent *U. pumila* trees have sustained serious branch damage. The "New Horizon" elms show only limited resistance to elm leaf beetle, and regular control measures may need to be considered in locations with severe or endemic elm leaf beetle in infestations. The "New Horizon" elm does, however, appear to be resistant to attack by the elm leaf miner *Fenusa ulmi*, an insect which over the past ten years has become a major pest on naturalized *U. pumila* and its hybrides with *U. rubra* or *U. glabra*.

What is claimed is:

1. A new and distinct variety of elm tree named "New Horizon" substantially as described and illustrated herein and characterized by its hardness, rapid growth, upright form and compact growth habit.

* * * * *